United States Patent
McCurdy et al.

(10) Patent No.: US 12,023,463 B2
(45) Date of Patent: Jul. 2, 2024

(54) CLINICAL NOTIFICATIONS

(71) Applicant: CERNER INNOVATION, INC., Kansas City, KS (US)

(72) Inventors: Michael McCurdy, Kansas City, KS (US); Matt R. Anderson, Kansas City, KS (US); Matthew Joseph Henkes, Lee's Summit, MO (US)

(73) Assignee: CERNER INNOVATION, INC., Kansas City, MO (US)

( * ) Notice: Subject to any disclaimer, the term of this patent is extended or adjusted under 35 U.S.C. 154(b) by 222 days.

(21) Appl. No.: 16/236,881

(22) Filed: Dec. 31, 2018

(65) Prior Publication Data

US 2019/0206577 A1   Jul. 4, 2019
US 2022/0262529 A9   Aug. 18, 2022

Related U.S. Application Data

(60) Provisional application No. 62/612,482, filed on Dec. 31, 2017.

(51) Int. Cl.
*H04L 67/55* (2022.01)
*A61M 5/14* (2006.01)
*G06F 3/0482* (2013.01)
*G16H 80/00* (2018.01)
*A61M 5/142* (2006.01)

(52) U.S. Cl.
CPC ............ *A61M 5/14* (2013.01); *G16H 80/00* (2018.01); *H04L 67/55* (2022.05); *A61M 2005/1402* (2013.01); *A61M 2005/14252* (2013.01); *G06F 3/0482* (2013.01)

(58) Field of Classification Search
CPC ........ G16H 80/00; H04L 67/26; G06F 3/0482
See application file for complete search history.

(56) References Cited

U.S. PATENT DOCUMENTS

| | | | | |
|---|---|---|---|---|
| 9,118,670 B2 * | 8/2015 | Martin | ................ | H04L 63/0861 |
| 2005/0246415 A1 * | 11/2005 | Belfiore | ................ | G06F 16/958 |
| | | | | 709/203 |
| 2008/0004502 A1 * | 1/2008 | Ash | ........................ | G16H 80/00 |
| | | | | 600/300 |
| 2011/0001605 A1 * | 1/2011 | Kiani | ..................... | G16H 40/67 |
| | | | | 235/492 |

(Continued)

FOREIGN PATENT DOCUMENTS

AU    2004209115 B2 *  4/2009  ............. G06Q 50/24

OTHER PUBLICATIONS

Moore et al., Event Detection: A Clinical Notification Service on a Health Information Exchange Platform, 2012 AMIA Annu Symp Proc 635-642 (Nov. 3, 2012) (Year: 2012).*

*Primary Examiner* — Jordan L Jackson
(74) *Attorney, Agent, or Firm* — Kraguljac Law Group, LLC

(57) ABSTRACT

Methods, computer systems, and computer-storage medium are provided for providing clinical information for a person, such as a test result, immediately and the information automatically and immediately pushed to the ordering physicians device. A graphical representation is generated for a clinician to select clinical notification options. The received selection creates a notification to be automatically sent to one or more clinician devices. Automatic notifications reduce delay in clinician action when new clinician information is provided.

20 Claims, 15 Drawing Sheets

(56) References Cited

U.S. PATENT DOCUMENTS

| | | | | |
|---|---|---|---|---|
| 2014/0280961 | A1* | 9/2014 | Martinez | H04L 41/5054 |
| | | | | 709/226 |
| 2015/0066525 | A1* | 3/2015 | Webb, III | G16H 10/60 |
| | | | | 705/2 |
| 2015/0096352 | A1* | 4/2015 | Peterson | F24F 11/33 |
| | | | | 73/31.02 |
| 2015/0149196 | A1* | 5/2015 | Ohad | G16H 70/00 |
| | | | | 705/2 |
| 2015/0149211 | A1* | 5/2015 | Ohad | H04L 67/1001 |
| | | | | 705/3 |
| 2015/0244687 | A1* | 8/2015 | Perez | G06F 21/604 |
| | | | | 726/4 |
| 2017/0262614 | A1* | 9/2017 | Vishnubhatla | G16H 50/20 |
| 2017/0372029 | A1* | 12/2017 | Saliman | G16H 10/60 |

* cited by examiner

FIG. 14.

CLINICAL NOTIFICATIONS

CROSS-REFERENCE TO RELATED APPLICATIONS

This application claims priority to U.S. Provisional Application 62/612,482, entitled "CLINICAL NOTIFICATIONS" and filed on 31 Dec. 2017, wherein the entirety of the application has been incorporated by reference herein.

BACKGROUND

Today, the speed at which individuals receive medical care is dependent upon manual processes. For instance, a patient's treatment is dependent upon the ordering physician's receipt of test results. This is typically accomplished one of three manual ways. First, the results are faxed to a physician. Second, test results are entered into an individual's electronic medical chart, such as an EMR, and the clinician logs into the electronic medical chart to view the results. Third, test results are delivered to the ordering physician or nurse by a telephone call.

For example, an MRI of the knee reveals a meniscus tear. The radiologist calls the ordering physician to provide results, and then dictates the report. The process is duplicate effort for the radiologist and requires phone availability from the ordering physician.

Each scenario delays care because it requires users to purposefully (and manually) retrieve or deliver results. Each manual process is time consuming, costly, and significantly delays treatment of the individual.

SUMMARY

Embodiments of the present invention provide methods and systems for performing providing clinical information for a person, such as a test result, immediately and the information automatically and immediately pushed to the ordering physician's Cerner-provisioned device(s) or personal device. It removes the manual processes that create bottlenecks in care today. Patients may begin treatment earlier, providing the greatest opportunity for positive outcomes.

Systems, methods and computer readable media for providing clinical notifications in a cloud-computing environment are described. Input by the control server is received for a sign on for a user clinician and identification of a person being treated by the user clinician. The control server automatically generates one or more graphical user interfaces for displaying a medical order screen for the person being treated or list of persons being treated by the clinician and at least a graphical representation of one or more user selectable clinical notification options. Input is received by the control server representing a user selection of one or more of the user selectable clinical notification options. The user selection is compared to a subsequent medical data received for the one or more persons being treated via the control server. The subsequent medical data is analyzed to determine if it satisfies the user selection of the clinical notification option. In response to determining if the subsequent medical data satisfies the user selection of the clinical notification option, the control server automatically generates in real time one or more graphical user interfaces for displaying the event notification of the subsequent medical data on a one or more clinician devices.

In one embodiment, input is received by the control server representing a user selection of a multiple medical devices selected to receive the clinical notification option. In this described embodiment in response to determining if the subsequent medical data satisfies the user selection of the clinical notification option, the control server displays an event notification on the multiple medical devices selected to receive the clinical notification option.

In some embodiments the event notification is filtered by the control server to remove the subsequent medical data about the one or more persons being treated by the user clinician. In some aspects, the medical order screen comprises a medical summary for the individual being treated by the clinician. In other aspects, the medical summary comprises patient vitas and measurements, reported symptoms, and prior diagnosis. The event notification in some aspects comprises critical alerts, vitals, and pathology results for the one or more persons being treated by the user clinician. The event notification may include subsequent medical data about the one or more persons being treated by the user clinician.

In one embodiment, the control server receives input representing a user selection of the clinical notification option and a multiple medical devices selected to receive the notification. When a clinical notification is generated, the control server automatically generates, in real time, one or more graphical user interfaces for displaying notification of data received for the person being treated on the multiple medical devices selected to receive the notification. In some embodiments, only one medical device may be selected to receive the notification.

A clinician may only want to be notified of critical results for an individual who they are treating but do not want non-critical results for the individual. This technology allows a medical worker to specify notification own to a patient, order and individual test result level so as not to over alert a medical worker. Additionally, the medical professional can specify devices for alerting. Each of these alerts occurring in real time, overcoming the slow process of traditional clinical notifications.

The clinical notification management application provides a system for clinicians and ancillary users to subscribe to, push, and receive notifications related to their role in medical treatment in real time. Notifications can be sent and received for clinical results for individuals being treated. Notifications can also be pushed to a clinician based on a change in status of patient encounters, appointments, or rooms. A user clinician can provide preferences to receive notifications based on individual encounters, patients, locations, lists, and date ranges.

The clinical notification management application in some embodiments, provides real time notifications of clinical information to clinicians and decreases delays in patient care. The clinical notification management application provides notifications outside of authenticated sessions (push notifications) without exposing protected health information (PHI) of individuals. This technology eliminates or reduces dependency of manual processes to communicate clinical results or status changes. In some embodiments the one or more graphical user interfaces with the subsequent medical data are displayed only when the user clinician authenticates on at least one of the multiple medical devices.

Unlike prior solutions, the clinician does not have to log into an individual's EMR or wait for a fax or telephone call to determine clinical information for the individual, such as test results. The clinical notification management application provides real time notifications of clinical information to clinicians and decreases delays in patient care. The clinical notification management application provides notifications outside of authenticated sessions (push notifications) without exposing protected health information (PHI) of individuals.

In some embodiments, when a user selects more than one medical devices to receive the clinical notification option the notification is sent to a selection of the multiple medical devices selected by the user. In some embodiments, the selection of multiple medical devices is determined by the control server based on device preference of the user. This can include information about the device including location. In other embodiments, a notification route is generated to deliver an event notification of the one or more clinician devices. The notification route may be generated by the control server in real time based on device data such as location of the device, date range, and notification type.

The claimed solution is necessarily rooted in computerized electronic medical relational database technology in order to overcome a problem specifically arising in the realm of computer medical clinical notification and communication. The claims address the problem of quickly and efficiently notifying a clinician of clinical information even when a user is not logged into an individual's electronic medical record.

The claimed system and method of the present application represents a new paradigm notifying clinicians in a real time manner. Not only does the claimed invention provide a way for a user to receive real time notifications of clinical results, the user can specify what user device to push notification. The user can also choose to receive notification when entering an order into an individual's electronic medical record.

The method and system for providing the user with the capability decide what notifications he/she wants to receive about what individuals and what devices to push the notifications. The clinical notification management application according to the new technology saves time and costs as clinical information is communicated to a user clinician in a manner defined by the user clinician.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

BRIEF DESCRIPTION OF THE DRAWINGS

Embodiments are described in detail below with reference to the attached drawing figures, wherein:

FIG. 14 is an interactive graphical user interface for a clinician to sign an order created for an individual.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

The present invention overcomes the delay in clinical notifications of previous clinical notification options. Previous clinical notification options rely on human interaction, sending alerts via phone calls and pagers by nurses or assistants. These notification options are slow because they require human oversight and input to contact clinicians and caregivers. Further, old notification options can be indiscrete—without verification the clinician is the one viewing what can be sensitive patient material. Embodiments of the present invention, however, allow users to select the notification to receive that is instantaneous and in real time. These notifications can be sent only to devices the user selects, or notifications can be sent to a selection of devices based on various data available to the control server. Further, notifications can be filtered from all sensitive medical data about a patient, only allowing a clinician to be notified of basic information such as results are in for a particular test. All of these features provide a faster, more reliable, and secure means to provide clinician notifications that overcome many of the failings of older notification solutions.

Figure 1:
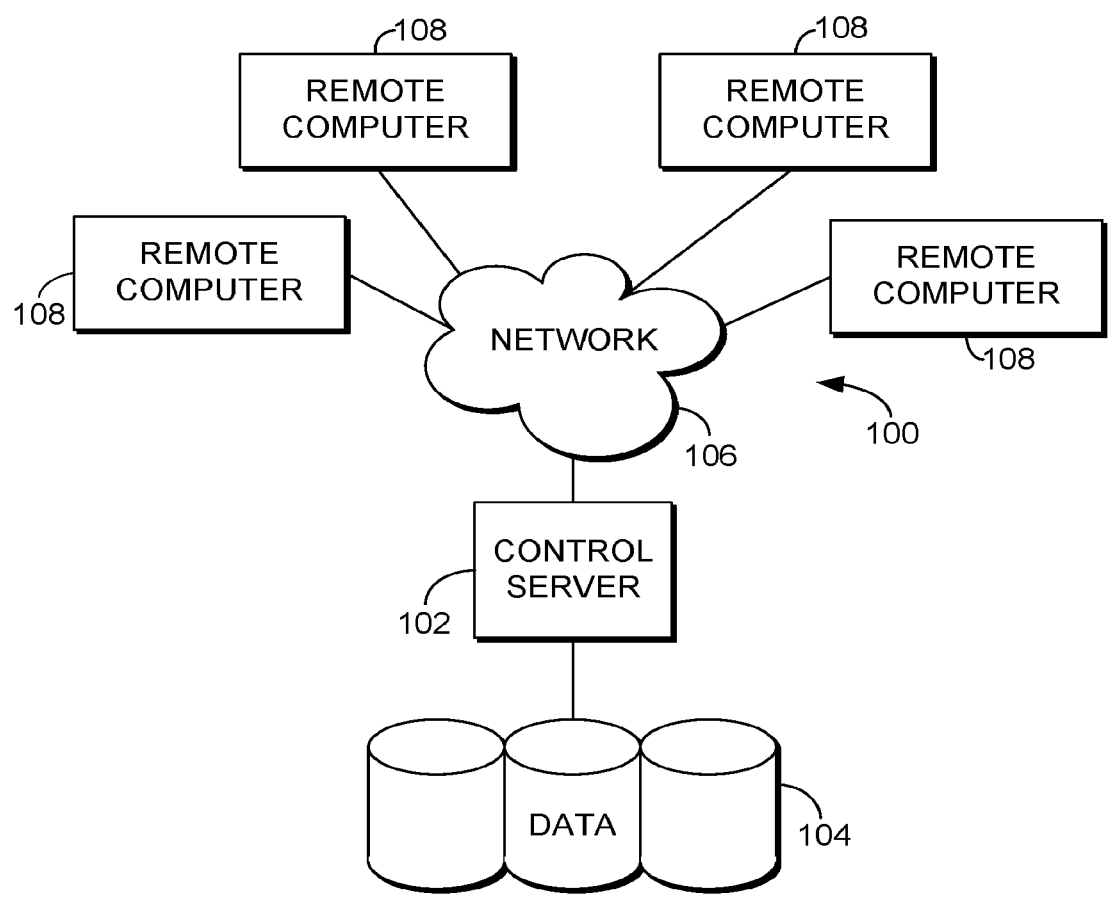
FIG. 1 is a block diagram of an exemplary computing environment suitable to implement embodiments of the present invention.

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
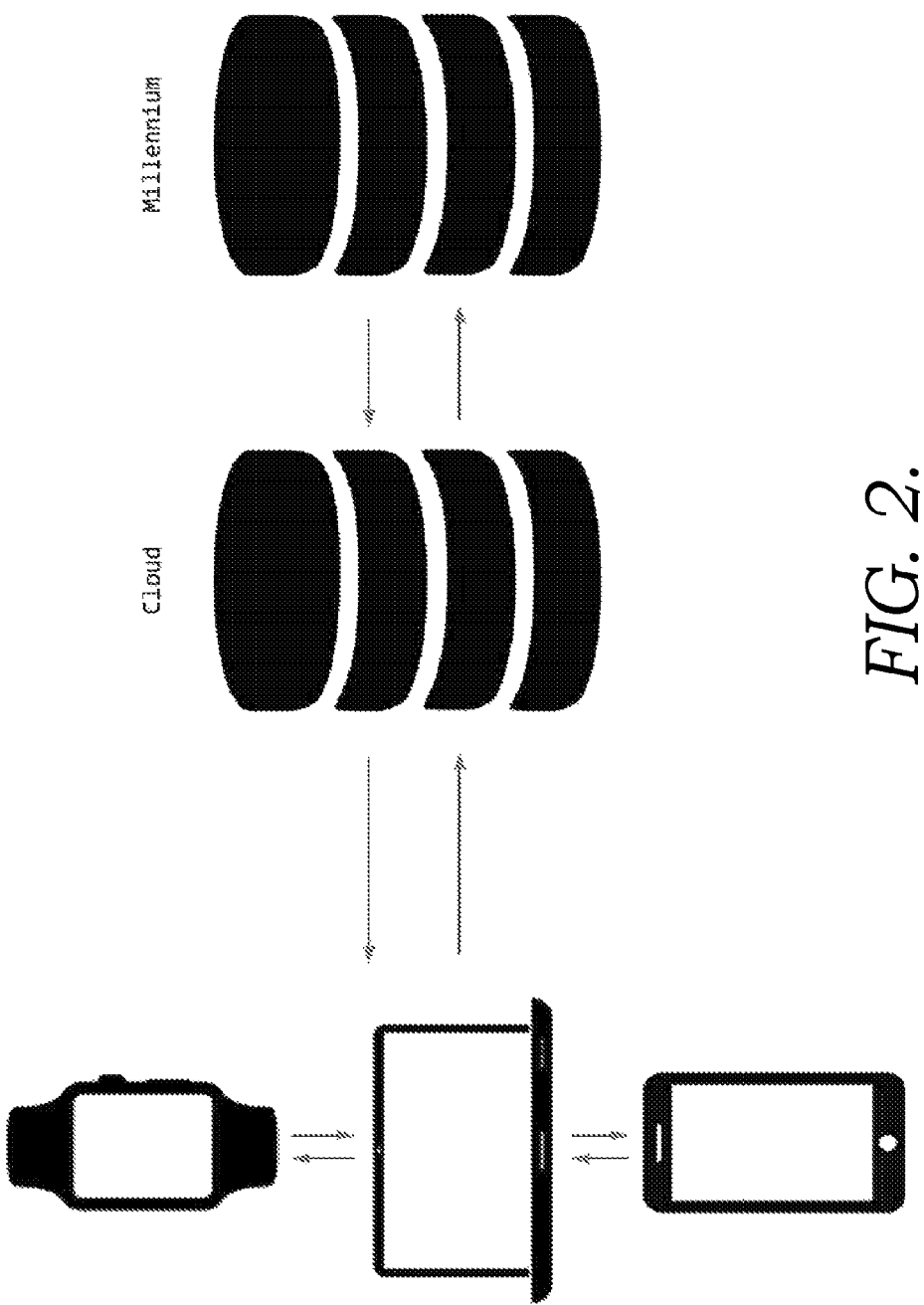
FIG. 2 is an exemplary system architecture suitable to implement embodiments of the present invention.

Embodiments of the present invention may be implemented in a cloud-computing environment as shown in FIG. 2. The cloud-computing network may comprise single or multiple servers running single or multiple virtual machines. In an embodiment exhibited by FIG. 2, a computer environment is depicted for managing and providing clinical notifications to a clinician for individuals being medically treated. Control server 102 hosts clinical notification management application in a cloud computing environment. Tasks performed by the processor utilize a variety of computer technology. In one embodiment, the control server are three tiers: a web server, application server and database server. Each tier is comprised of a number of system layers as described below.

Figure 3:
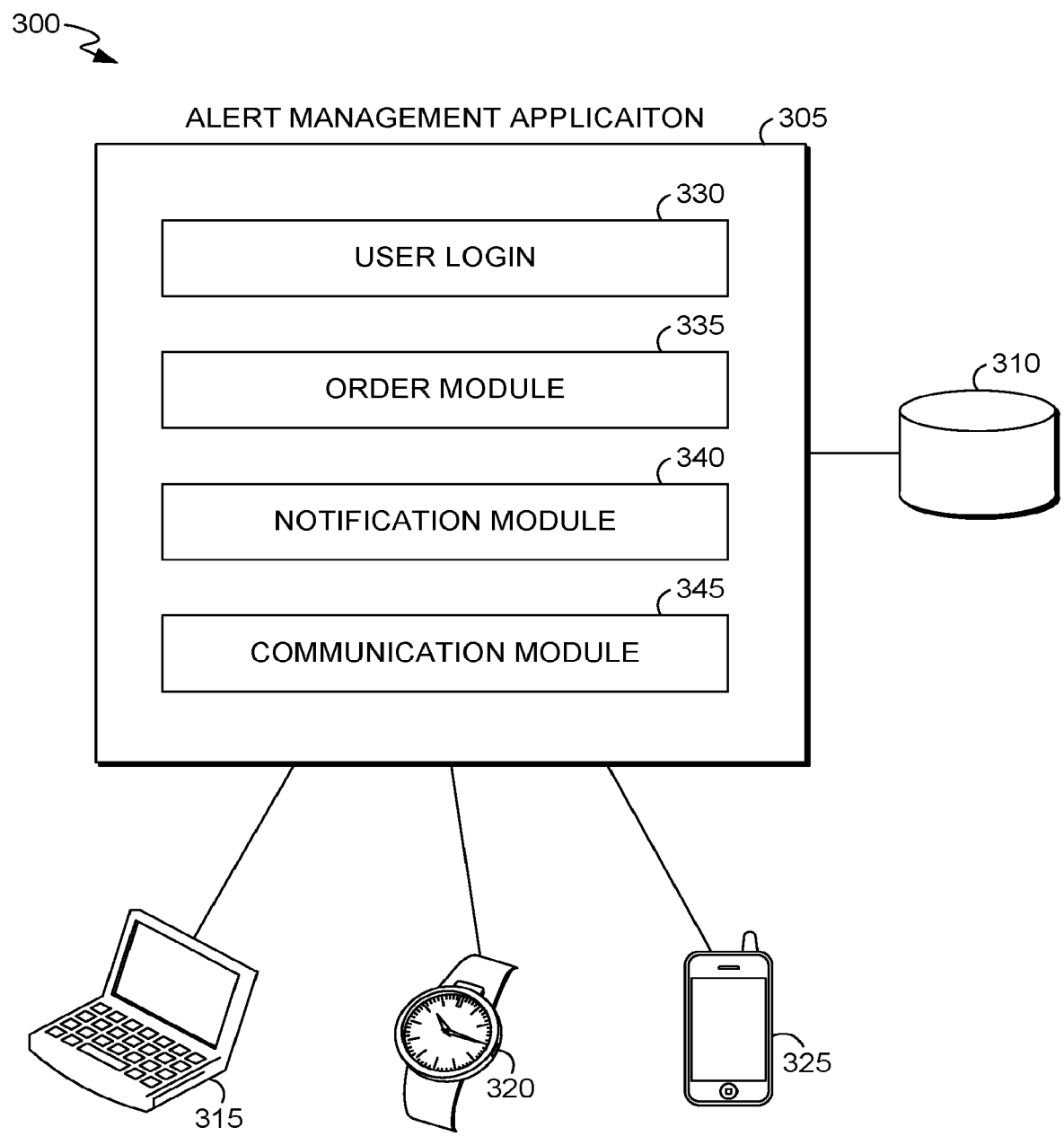
FIG. 3 is an exemplary system architecture suitable to implement embodiments of the present invention.

As shown in FIG. 3, a clinical notification system 300 includes a client server 310, such as Cerner Millennium, with active relational database files is located in a location such as a pharmacy, hospital system servers in a cloud-computing environment. Clinical notification management application 305 resides on a control server and is in communication with multiple clinician devices 315, 320 and 325 to provide notifications to the clinician according to the clinician's subscription preferences via a network (not shown). A network, such as the internet or other public or private network, serves as a communications link from clinical notification management application 305, a relational database EMR 310, such as Millennium and clinician devices 315, 320 and 325.

Clinician notifications are managed and transmitted by clinical notifications management application 305 on a control server in a cloud-computing environment in a timely, efficient and secure manner using embodiments of the present invention. Clinical notification management application 305 manages notification subscriptions, pushes notifications, and processes read receipts. Clinical notification management application 305 includes user login 330, order module 335, notification module 340 and communication module 345.

User login 330 allows the user to log into the clinical notification management application 305. A user may login directory to the clinical notification management application 305 or may be indirectly logged into the clinical notification management application 305 by logging into the client server hosting the EMR. In some embodiments, medical data collected are displayed only when the user clinician authenticates on at least one of the multiple medical devices.

The order module manages clinical result for individuals, changes in status for individuals being treated and errors relating the individual medical chart modifications. Notification module 340 manages clinician notification subscription by providing user selectable notification options to the clinician via communication module 345. The subscription notification preferences can include the relationship between the clinician and individual being medically treated (e.g., doctor patient relationship). The subscriptions can also be based on location of the individual (e.g., the ward of the medical facility) or location of the clinician (e.g., in the medical facility or outside the medical facility). The subscriptions can be made by the clinician at the time of encounter. For example, while the clinician is placing an order for the individual in the EMR, the clinician can select user selectable options to be notified of all or part of the results from the order being placed.

The clinician can also choose notifications based for a particular date range for an individual or group of individuals. The clinician can further subscribe to notification based on result type such a radiology, lab, pathology and/or results that are critical versus non-critical results. The type of result can be designated for an individual, multiple individuals or an individual being treated by the clinician. For things not specified, the clinical notification management application allow a clinician to "ad hoc" subscribe for notifications not specifically provided for.

In some embodiments, the local database of the notification module stores the clinician notification preferences. The notification module monitors clinical data for the individual being communicated to the individual's EMR. The notification module compares the clinician notification preferences to clinical data for the individual, and if one or more of the clinician notification preferences is satisfied, the communication module 345 communicate the notification to the preferred clinician device(s) 315-325. In other embodiments, the communication module determines a notification route to deliver the notifications to a selection of medical devices. The communication module may take into account several factors when making this determination, including the location of the clinician devices, date range, priority, and notification type. This determination is advantageous to provide sufficient notification to the clinician without over alerting the clinician. Sending too many notifications can cause a clinician not to check the clinical device for updates.

The clinician and clinician devices are registered with the clinician notification management application by querying a database of clinician or direct registration by the clinician. A user with authority can access the authorized individual medical treatment electronic records and can register with the clinical notification management application to receive notification regarding the individual and/or electronic record. The clinical notifications management application provides graphical user interfaces via communication module to one or more clinician devices. User clinicians choose from user selectable options to select notifications they want to receive and on what devices.

Figure 4:
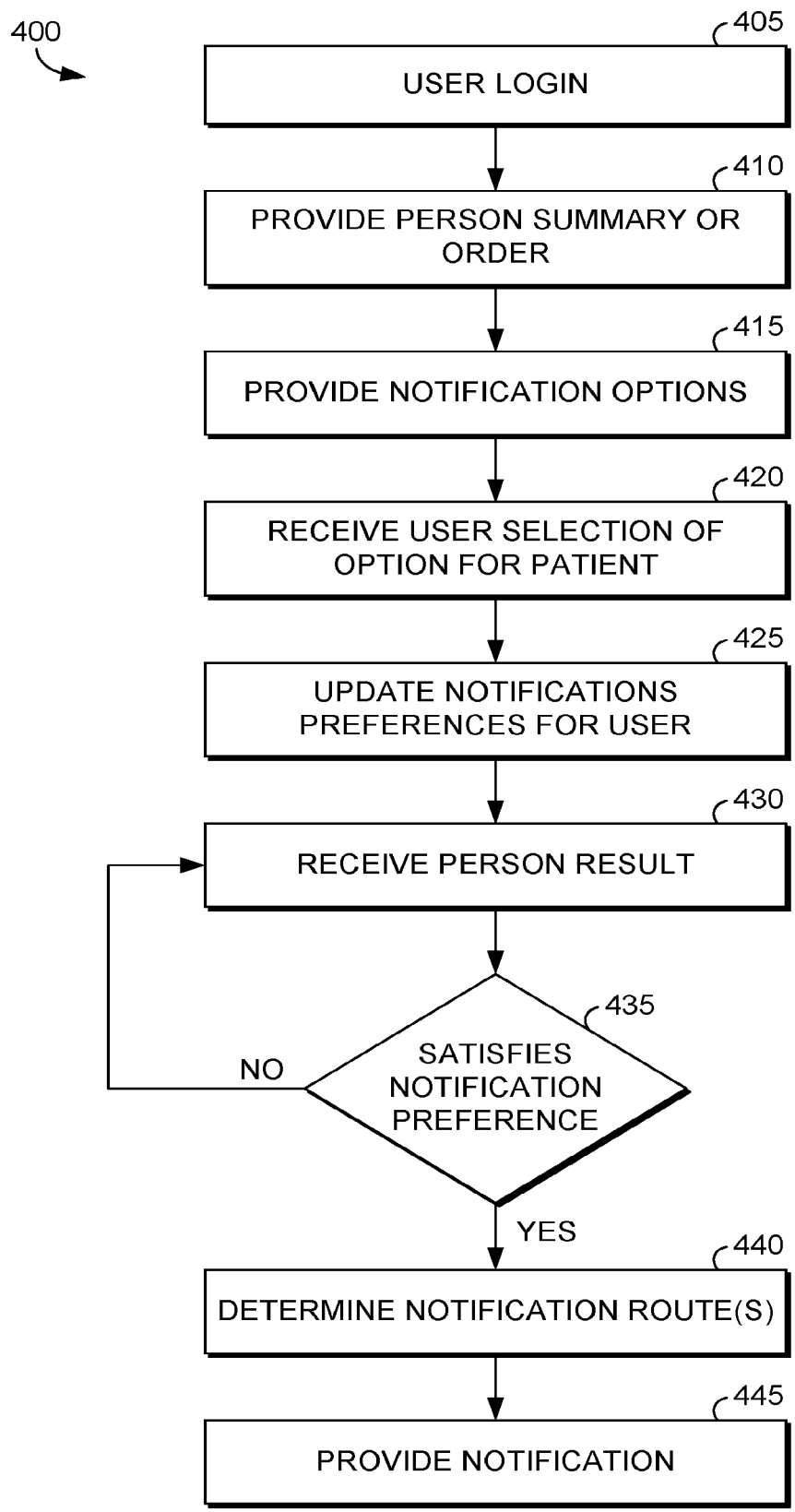
FIG. 4 is a flow diagram depicting a process to provide clinical notifications to a clinician.

Referring next to FIG. 4, a method 400 for providing coordinated clinical messages to a clinician is provided. At step 405, a user clinician logs into the clinical notification management application directly or indirectly through an EMR system.

At step 410, in some embodiments a medical summary for an individual being treated by the clinician or order entry screen for the individual are provided to a clinician. These interactive graphical user interfaces are displayed on a variety of user devices included a smart phone, laptop, smart watch and personally. At step 415, user selectable notification options are provided to the clinician to select notifications. The user selectable options can be provided generally to a clinician or while a clinician is viewing an individual's medical summary or in conjunction with a medical order entry interactive graphical user interface as shown in FIGS. 6-14.

Continuing with FIG. 4, at step 420, the clinical notification management application receives selection of the clinician of criteria to notify the clinician. Other information that may be selected by the user clinician includes what user device to notify. The user selectable options can include the relationship between the clinician and individual being medically treated (e.g., doctor patient relationship). The subscriptions can also be based on location of the individual (e.g., the ward of the medical facility) or location of the clinician (e.g., in the medical facility or outside the medical facility). The subscriptions can be made by the clinician at the time of encounter. For example, while the clinician is placing an order for the individual in the EMR, the clinician can select user selectable options to be notified of all or part of the results from the order being placed.

The clinician can also choose notifications based for a particular date range for an individual or group of individuals. The clinician can further subscribe to notification based on result type such a radiology, lab, pathology and/or results that are critical versus non-critical results. The type of result can be designated for an individual, multiple individuals or an individuals being treated by the clinician.

In one use case, a physician or nurse selects to be notified on all personal user devices regarding all information a person in his/her treatment so that the clinician can treat the patient as quickly as possible. In another use case, an ambulatory physician or nurse selects user options to be notified with status updates on the clinician laptop, phone or watch so the clinician knows when a patient is ready to be seen.

In another example, a clinician is electronically charting for a patient and needs to be aware of error notifications in the patient's chart that have not successfully been saved so the clinician can take corrective action. In another case, a clinician wants to set results alerts to be provided notifications related to a particular encounter, patient, or list so that clinician can treat or consult on a patient faster. Additional notifications include providing notifications to an acute care bed management user, receiving notifications on his or her laptop, phone, or watch when a bed is available for use.

At step 425, the clinician user preferences are stored in a local database of the clinical notification management application. The user preferences can be specific to the user and to the individual(s) the user clinician is treating. At step 430, clinical data, such as test results for an individual are received and evaluated to see if they satisfy user notification preference. This clinical data may be subsequent medical data received after the clinician user preferences are received. The clinical data could be information specific to an individual patient, a department or information related to charting patient information. At step 435, it is determined whether the result satisfies the notification preference. If the personal result from step 430 does not satisfy the notification preference at step 435, then the process repeats for a subsequent personal result. If step 435 is satisfied, then the control server may proceed to step 440. At step 440, the control server determines a notification route to provide the alert to the clinician selected medical devices. In some embodiments, the notification route may be to send an alert to a selection of devices based on a number of factors about the device, such as the location, date range, priority, and type of notification. At step 445 the notification is provided to the device.

Figure 5:
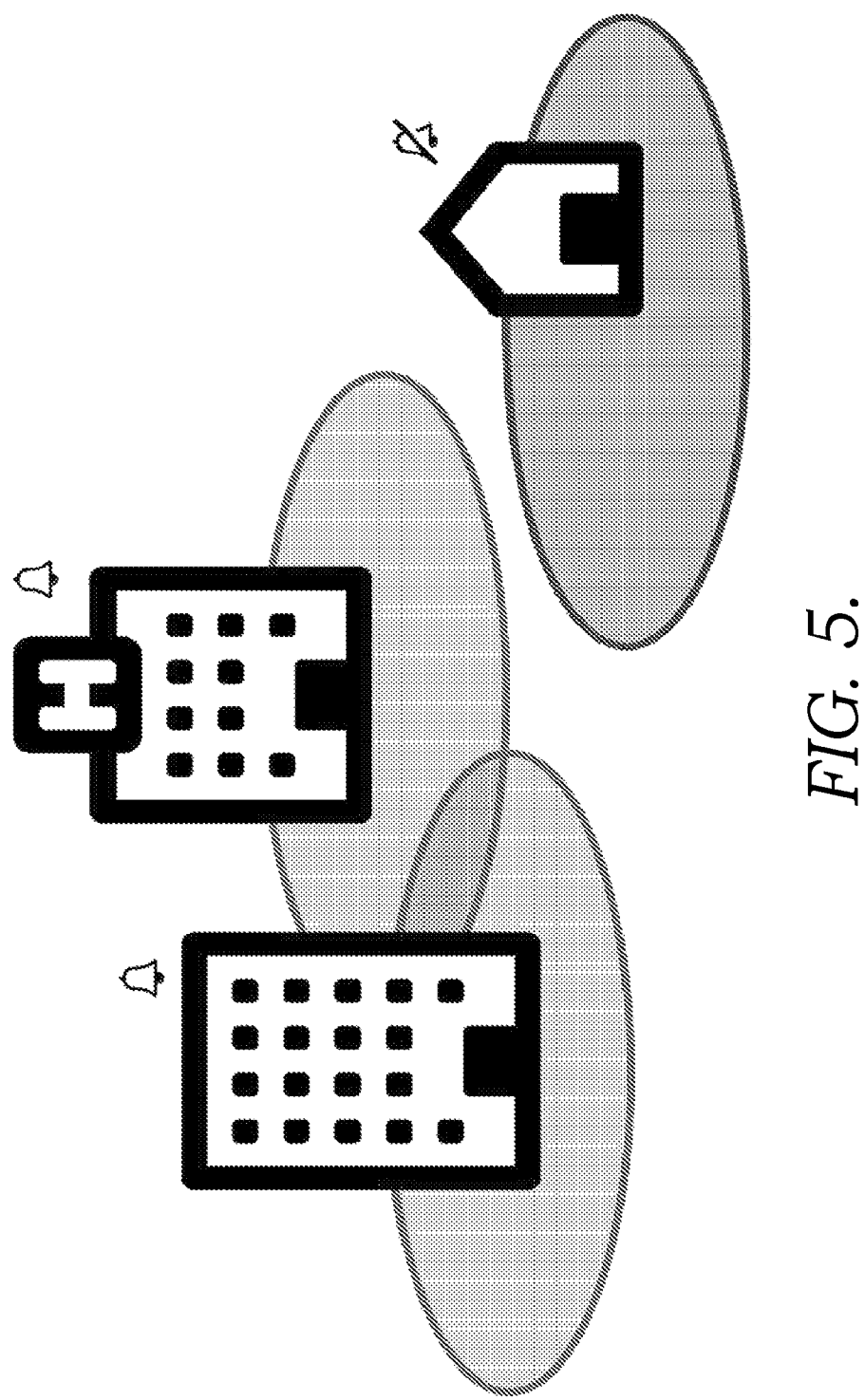
FIG. 5 is an exemplary block diagram depicting where clinical notifications are to be provided to a clinician.

For example, FIG. 5, if the user clinician is logged in at a medical facility the user clinician may select to only be notified at the medical facility and not on his or her personal device. And therefore the notification route will only send the messages to the medical facility and not the his or her personal device. However, if the clinician is not located at the medical facility, the clinician may want to receive notifications on his or her personal smart phone, tablet or laptop. In another example, in embodiments where the notification route selects one device from the user selected medical devices and the medical devices include personal devices, the notification route may determine not to provide notifications to the users personal device. The control server based on time of day and location of devices will determine that notifications should be provided to the medical devices at the medical facility to alert the clinician.

Figure 6:
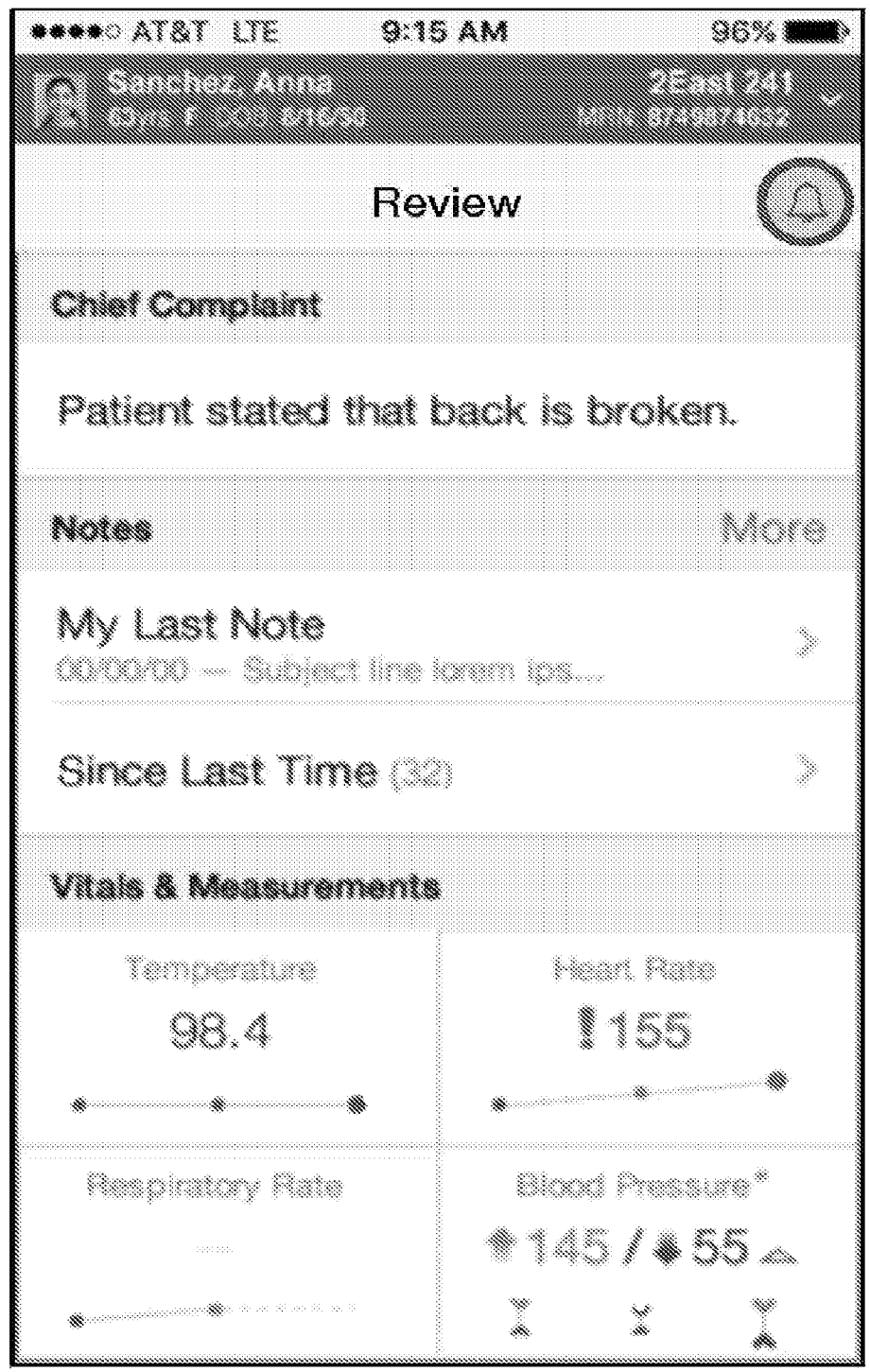
FIG. 6 is an interactive graphical user interface depicting a medical summary of an individual to a clinician.

With reference to FIG. 6, an interactive graphical user interface on a user clinician's personal device is shown. The graphical user interface includes a medical summary for an individual being treated by the clinician. The user can select the "alert" icon in the top right corner to select notification options for this individual.

Figure 7:
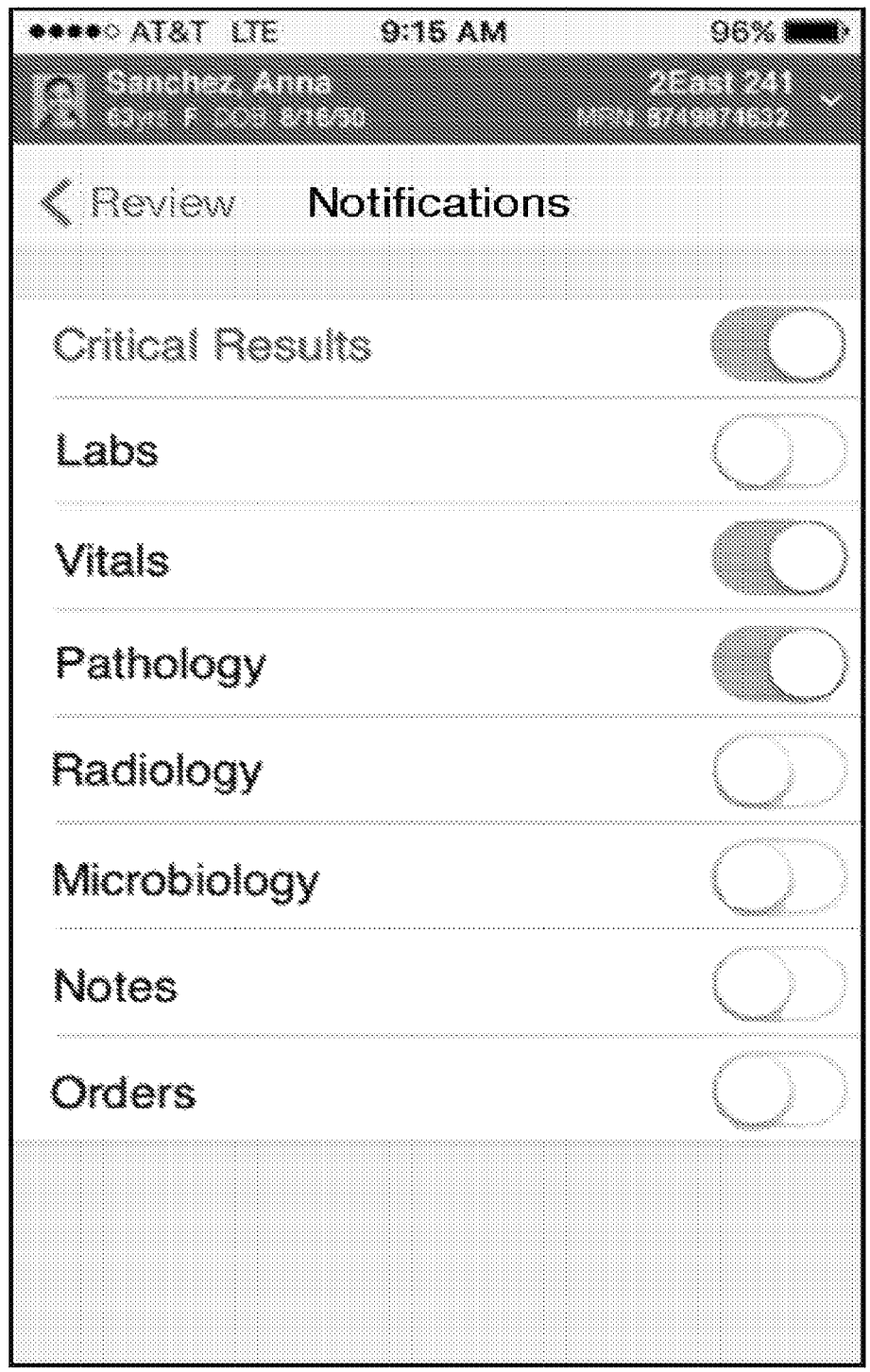
FIG. 7 is an interactive graphical user interface displaying user selectable notification options for an individual to a clinician.

FIG. 7 is an interactive graphical user interface that includes user selectable notification options. From this interface, the user clinician can select the types of notifications such as critical alerts, vitals and pathology results for this individual. Once selected, these user notifications preferences are stored and screened by the clinical notification management application.

Figure 8:
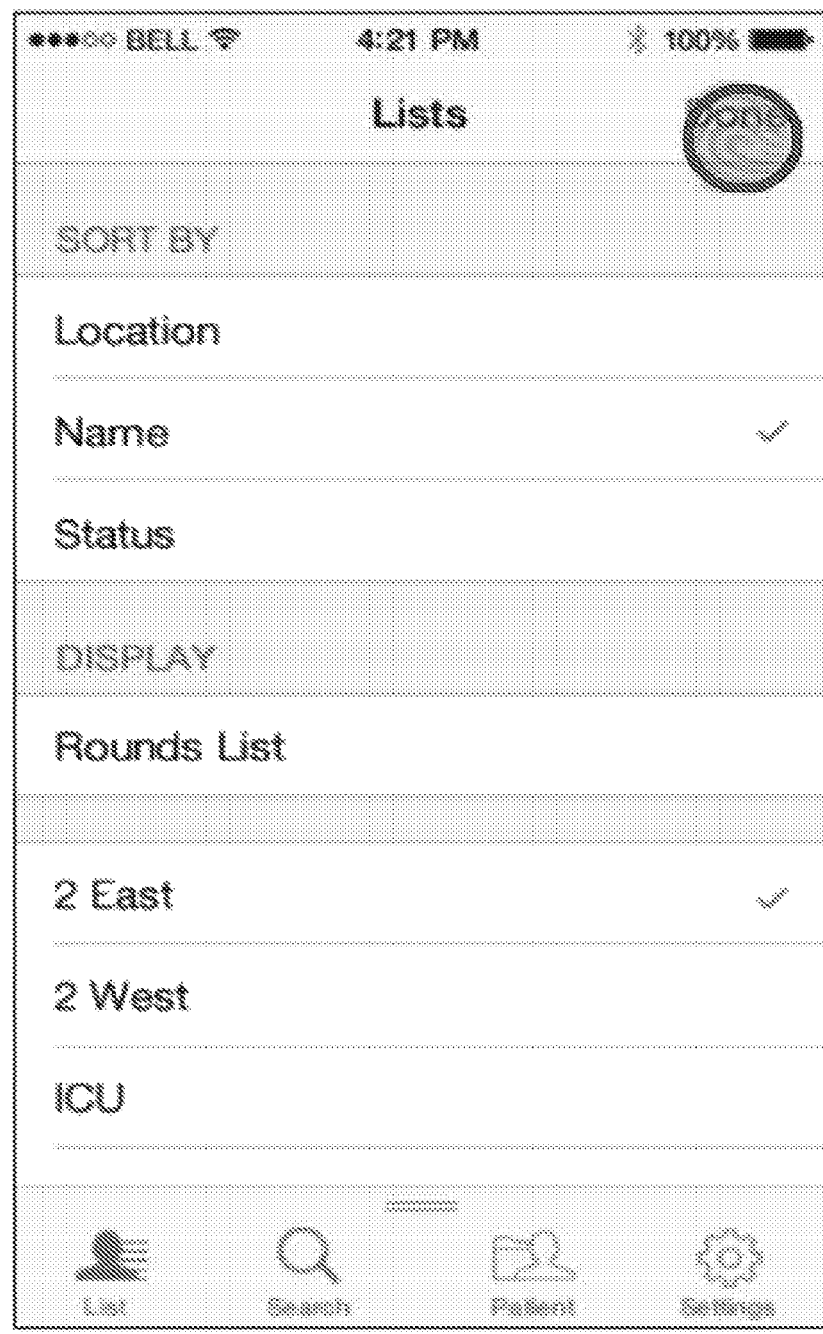
FIG. 8 is an interactive graphical user interface displaying user selectable options for a list of individuals being treated.
Figure 9:
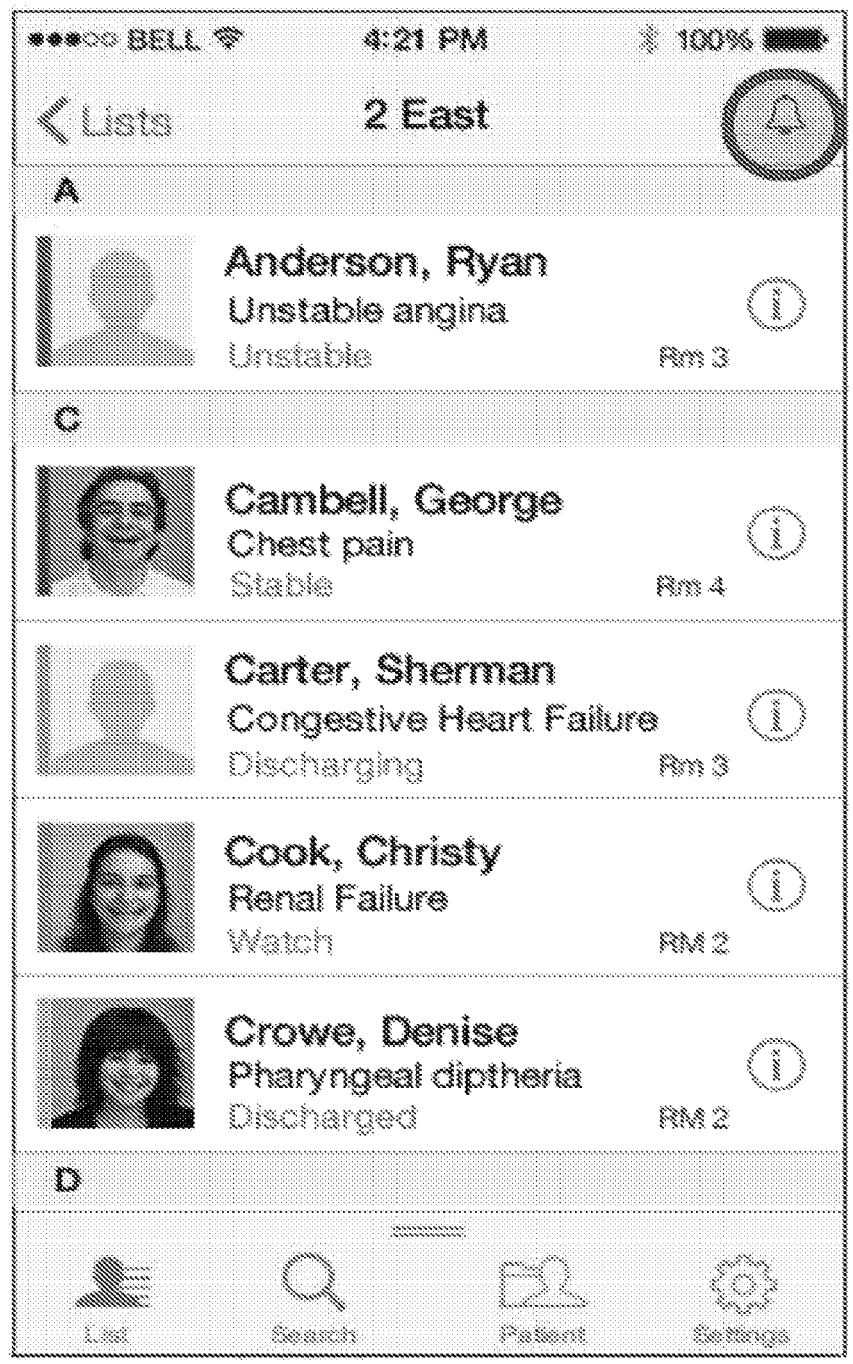
FIG. 9 is an interactive graphical user interface displaying user selectable options of individuals being treated.

FIG. 8 is an interactive graphical user interface that includes user selectable options to view a list of the user clinician's patients in a particular location, ward 2 East as shown in FIG. 9. From FIG. 9, the user can select the "alert" icon in the top right corner to select notifications for this group of individuals.

Figure 10:
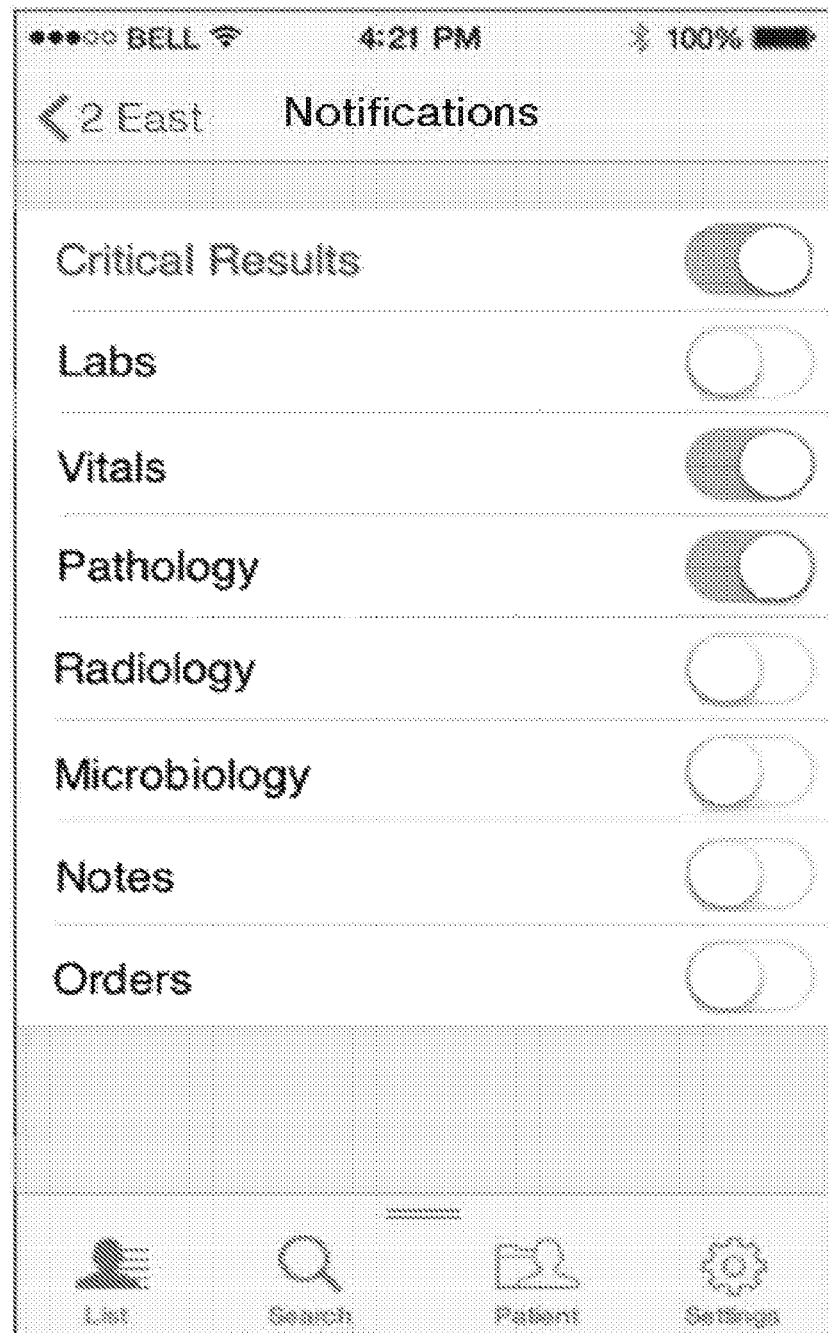
FIG. 10 is an interactive graphical user interface displaying user selectable notification options for individuals being treated.

FIG. 10 is an interactive graphical user interface that includes user selectable notification options. From this interface, the user clinician can select the types of notifications for this group of patients. The user clinician selects to receive notifications for critical alerts, vitals and pathology result for the individuals in this group.

Figure 11:
FIG. 11 is an interactive graphical user interface with an order summary for an individual.
Figure 12:
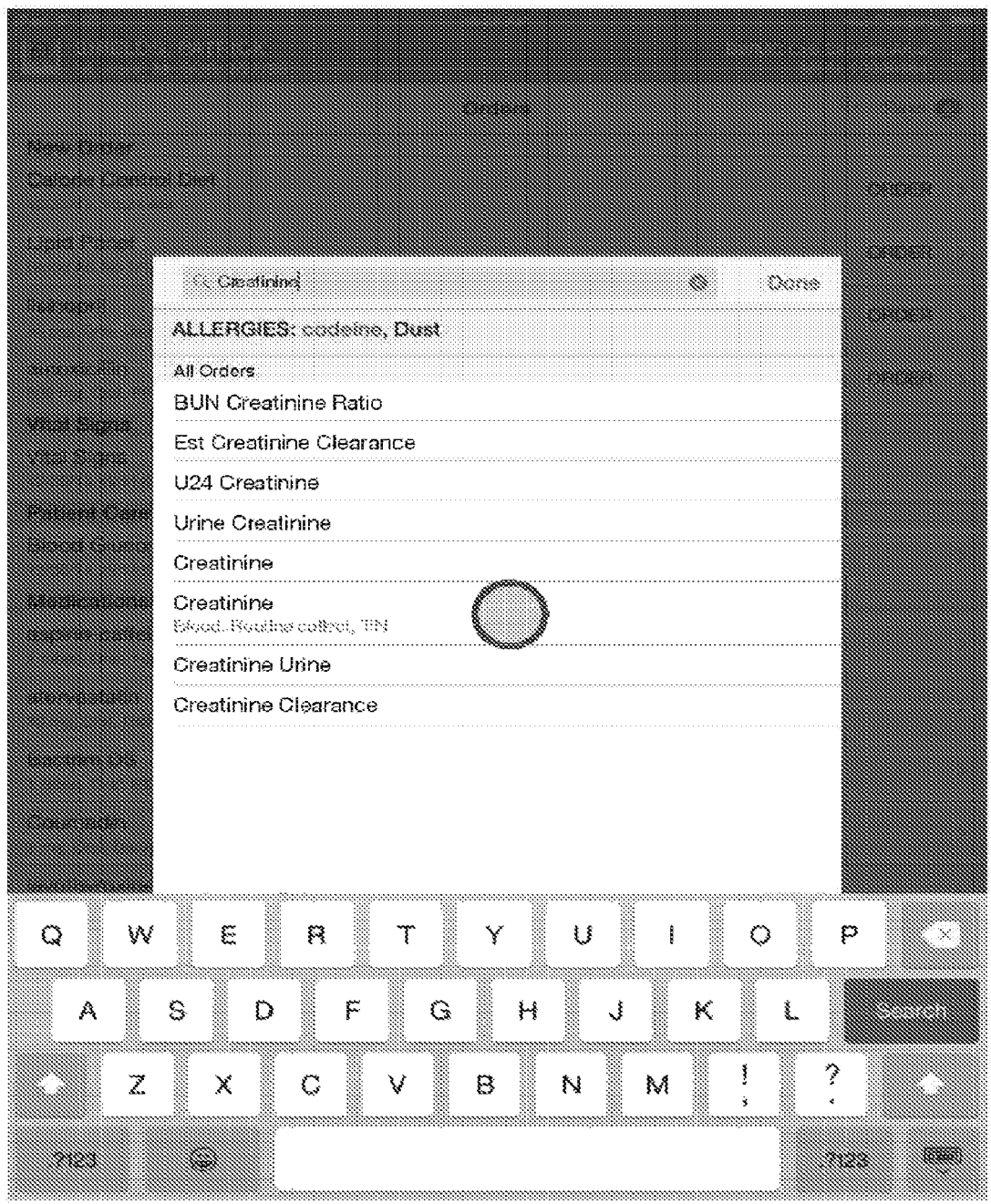
FIG. 12 is an interactive graphical user interface for a clinician to create an order for an individual.
Figure 13:
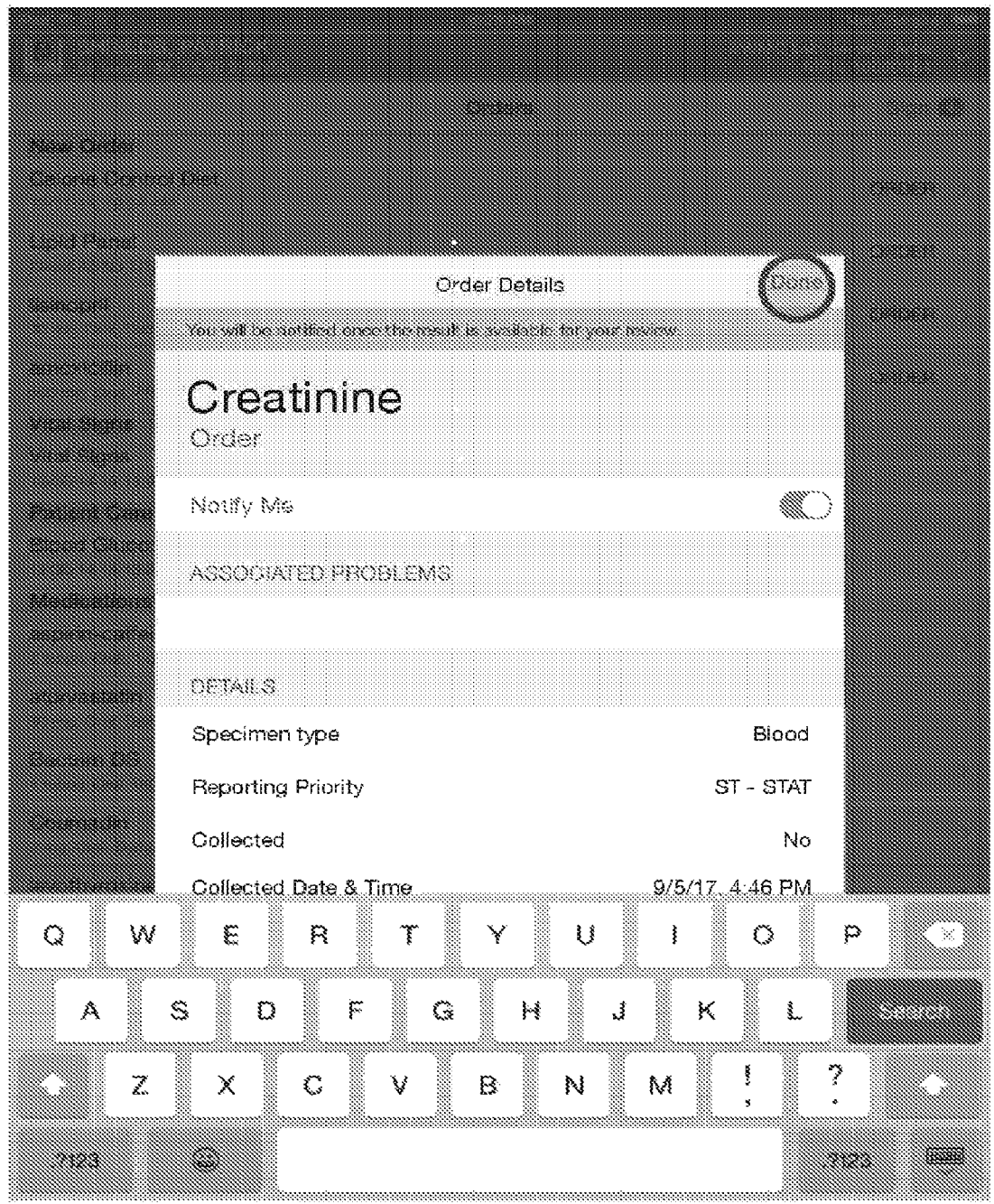
FIG. 13 is an interactive graphical user interface for a clinician to select notifications of results from an order being created.

FIG. 11 is an interactive graphical user interface that displays to a clinician an order summary for a patient being treated. The user can select the option to create a new order for the patient and sign and place orders from this graphical user interface. From the graphical user interface, the user selects to create a new creatine order as shown in the pop up screen of FIG. 12. In the graphical user interface of FIG. 13, the user can choose from the order details whether to be notified of the results.

Figure 14:
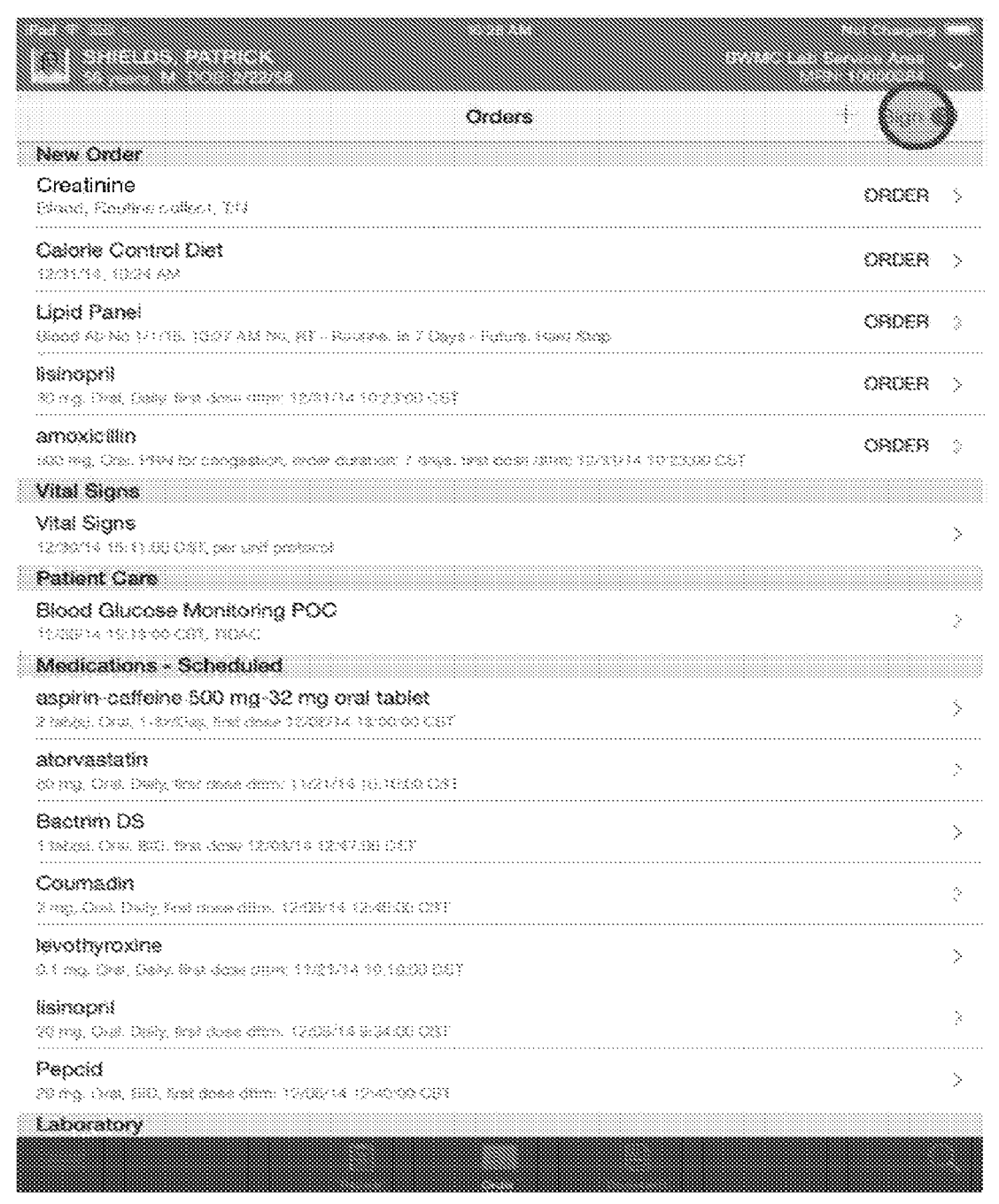
Figure 15:
FIG. 15 is an interactive graphical user interface for displaying notifications to a clinician.

In FIG. 14, the user signs the order for a creatine lab tests in the upper right hand corner. The selection of the notification preference is stored and monitored by the clinical notification management application as described above. When the application determines that the results for the creatine order have been received, a notification of creatine results is sent to the user clinician's device as shown in FIG. 15 (previously specified by user). As can be seen in FIG. 15, the clinician is notified that results are available but no HIPAA private information is displayed. After receiving the notification, the user clinician can access a secure and private application to view the actual result information for the patient while maintaining privacy for the individual.

The present invention has been described in relation to particular embodiments, which are intended in all respects to be illustrative rather than restrictive. Further, the present invention is not limited to these embodiments, but variations and modifications may be made without departing from the scope of the present invention.

The invention claimed is:

1. One or more non-transitory computer-readable media having computer-executable instructions embodied thereon that, when executed, perform a computerized method for providing a clinical notification, the computerized method comprising:

receiving a first input via a cloud computing network that hosts a control server managing a clinical notification management application, wherein the first input causes a login into the clinical notification management application, the first input corresponding to a user clinician and identification of one or more persons being treated;

in response to logging into the clinical notification management application, automatically generating, via the control server, one or more graphical user interfaces that display a medical order screen having a clinical notification option that identifies notification preferences corresponding to (1) the one or more persons being treated and (2) a computing device for receiving clinical notifications;

receiving a second input, via the one or more graphical user interfaces and the control server, representing a user selection that defines the clinical notification option including at least a type of medical result data being an error relating to a patient medical chart for which a clinical notification will be generated;

monitoring subsequent medical data that is received into one or more electronic medical records (EMR) associated with the one or more persons being treated;

determining whether the subsequent medical data received via the electronic medical records (EMR) for the one or more persons being treated includes data that matches the notification preferences stored by the control server including the type of medical result data to satisfy the user selection of the clinical notification option; and in response to determining the subsequent medical data satisfies the user selection of the clinical notification option, automatically generating in real-time, via the control server, the one or more graphical user interfaces that display the clinical notification on the computing device corresponding to the user selection.

2. The media of claim 1, further comprising executable instructions for receiving a third input, via the control server, representing a notification device preference of the computing device to display the clinical notification, the notification device preference corresponding to an encounter between the user clinician and the one or more persons being treated and a location of the one or more persons.

3. The media of claim 1, further comprising executable instructions for automatically generating, via the control server, a notification route to deliver the clinical notification to a plurality of computing devices, wherein the notification route is based on a location of the plurality of computing devices and a priority of the clinical notification.

4. The media of claim 3, wherein the notification route is automatically generated via the control server in real time based on a clinician device data.

5. The media of claim 1, wherein the clinical notification option comprises critical alerts, vitals and pathology results as selectable options.

6. The media of claim 4, wherein the clinical notification option comprises a date range and a notification type.

7. The media of claim 1, wherein the clinical notification is filtered by the control server to remove sensitive medical data about the one or more persons being treated.

8. A computer-implemented method in a clinical computing environment for providing a clinical notification, the method comprising:
   receiving a first input via a cloud computing network that hosts a control server managing a clinical notification management application, wherein the first input causes a login into the clinical notification management application, the first input corresponding to a user clinician wherein the user clinician is associated with one or more persons being treated by the user clinician;
   in response to logging into the clinical notification management application, automatically generating, via the control server, one or more graphical user interfaces that display a medical order screen having a clinical notification option that identifies selectable notification preferences that is assigned to (1) the one or more persons being treated and (2) multiple medical devices for receiving clinical notifications;
   receiving a second input, via the one or more graphical user interfaces and the control server, representing a user selection that defines the clinical notification option including at least a type of medical result data including an error relating to a patient medical chart for which a clinical notification will be generated and selects one or more devices of the multiple medical devices to receive the clinical notification;
   monitoring subsequent medical data that is received into one or more electronic medical records (EMR) associated with the one or more persons being treated;
   determining whether the subsequent medical data received via the electronic medical records (EMR) for the one or more persons being treated includes data that matches the notification preferences stored by the control server including the type of medical result data to satisfy the user selection of the clinical notification option; and
   in response to determining the subsequent medical data satisfies the user selection of the clinical notification option, automatically generating in real-time, via the control server, the one or more graphical user interfaces that display the clinical notification on the one or more devices of the multiple medical devices selected to receive the clinical notification.

9. The method of claim 8, wherein the medical order screen comprises a medical summary for one of the one or more persons being treated by the user clinician.

10. The method of claim 9, wherein the medical summary comprises patient vitals and measurements, reported symptoms, and a prior diagnosis.

11. The method of claim 8, wherein the clinical notification comprises critical alerts, vitals and pathology results for the one or more persons being treated by the user clinician.

12. The method of claim 8, wherein the clinical notification includes the subsequent medical data about the one or more persons being treated by the user clinician, and wherein logging into the clinical notification management application comprises logging into the control server hosting the EMR.

13. The method of claim 12, wherein the one or more graphical user interfaces with the subsequent medical data are displayed only when the user clinician authenticates on at least one of the multiple medical devices.

14. A system for providing a clinical notification, the system comprising:
   one or more processors; and
   one or more computer storage media storing instructions that, when used by the one or more processors, cause the one or more processors to:
   receive a first input, via a cloud computing network that hosts a control server managing a clinical notification management application, wherein the first input causes a login into the clinical notification management application, the first input corresponding to a user clinician and one or more persons being treated by the user clinician;
   in response to logging into the clinical notification management application, automatically generate, via the control server, one or more graphical user interfaces that display a medical order screen having a clinical notification option that is assigned to (1) the one or more persons being treated and (2) multiple medical devices for receiving clinical notifications;
   receive a second input, via the one or more graphical user interfaces and the control server, representing a user selection that defines the clinical notification option including notification preferences including at least a type of medical data for which a clinical notification will be generated and selects one or more of the multiple medical devices to receive the clinical notification;
   wherein the type of medical result data includes an error relating to a patient medical chart;
   monitor subsequent medical data that is received into one or more electronic medical records (EMR) associated with the one or more persons being treated;
   determine whether the subsequent medical data received via the electronic medical records (EMR) for the one or more persons being treated includes data that matches the notification preferences stored by the control server including the type of medical data to satisfy the user selection of the clinical notification option; and
   in response to determining the subsequent medical data satisfies the notification preferences of the clinical notification option, automatically generate in real-time, via the control server, the one or more graphical user interfaces that display the clinical notification on the one or more devices of the multiple medical devices selected to receive the clinical notification.

15. The system of claim 14, further comprising the one or more computer storage media storing instructions that, when used by the one or more processors, cause the one or more processors to receive a third input via the one or more graphical user interfaces and the control server representing a notification device preference of the multiple medical devices to display the clinical notification.

16. The system of claim 14, further comprising the one or more computer storage media storing instructions that, when used by the one or more processors, cause the one or more processors to automatically generate via the control server a notification route to deliver the clinical notification to the multiple medical devices selected to receive the clinical notification.

17. The system of claim 14, further comprising the one or more computer storage media storing instructions that, when used by the one or more processors, cause the one or more processors to configure the clinical notification option to include selectable options for critical alerts, vitals and pathology results for which the clinical notification will be generated.

18. The system of claim 14, further comprising the one or more computer storage media storing instructions that, when used by the one or more processors, cause the one or more processors to automatically generate a notification route via the control server in real time based on a clinician device data to deliver the clinical notification to the one or more devices of the multiple medical devices selected to receive the clinical notification.

19. The system of claim 14, wherein the medical order screen comprises a medical summary for one of the one or more persons being treated by the user clinician, and wherein the medical summary comprises patient vitals and measurements, reported symptoms, and a prior diagnosis.

20. The system of claim 14, wherein the notification preferences comprise a location of the multiple medical devices, a date range, and a notification type, and wherein the clinical notification is a push notification.

* * * * *